United States Patent [19]

Walker et al.

[11] Patent Number: 4,728,322

[45] Date of Patent: Mar. 1, 1988

[54] ADJUSTABLE CATHETER ASSEMBLY

[75] Inventors: Jack M. Walker, Portola Valley; Neil J. Sheehan, Emmeryville, both of Calif.

[73] Assignee: Menlo Care, Inc., Palo Alto, Calif.

[21] Appl. No.: 826,439

[22] Filed: Feb. 5, 1986

[51] Int. Cl.$^4$ .............................................. A61M 5/00
[52] U.S. Cl. ................................... 604/165; 604/164; 604/265
[58] Field of Search ............... 604/165, 265, 283, 264, 604/280, 164, 240, 158, 905; 128/343; 528/904; 521/905

[56] References Cited

U.S. PATENT DOCUMENTS

| | | | |
|---|---|---|---|
| 3,537,451 | 11/1970 | Beck et al. | 604/165 |
| 3,589,361 | 6/1971 | Loper | 604/165 |
| 3,592,192 | 7/1971 | Harsutuneian | 604/165 |
| 3,595,230 | 7/1971 | Suyeoka et al. | 604/164 |
| 3,766,916 | 10/1973 | Moorehead et al. | 604/165 |
| 3,769,975 | 11/1973 | Nimoy et al. | 604/165 |
| 3,822,238 | 7/1974 | Blair | 521/905 |
| 3,975,350 | 8/1976 | Hudgin et al. | 521/905 |
| 4,106,491 | 8/1978 | Guerra | 604/169 |
| 4,177,809 | 12/1979 | Moorehead | 604/165 |
| 4,183,884 | 1/1980 | Wichterle et al. | 264/41 |
| 4,192,304 | 3/1980 | Millet | 604/250 |
| 4,192,305 | 3/1980 | Seeberg | 604/165 |
| 4,194,504 | 3/1980 | Harms et al. | 604/164 |
| 4,198,973 | 4/1980 | Millet | 604/165 |
| 4,239,042 | 12/1980 | Asai | 604/164 |
| 4,300,553 | 11/1981 | Seberg | 604/165 |
| 4,326,519 | 4/1982 | D'Alo et al. | 604/165 |
| 4,353,369 | 10/1982 | Muetterties et al. | 604/272 |
| 4,388,074 | 6/1983 | Seberg et al. | 604/165 |
| 4,389,210 | 6/1983 | Genese | 604/177 |
| 4,411,655 | 10/1983 | Schreck | 604/165 |
| 4,434,797 | 3/1984 | Silander | 604/264 |
| 4,445,893 | 5/1984 | Bodicky | 604/165 |
| 4,581,019 | 4/1986 | Curelaru et al. | 604/165 |

FOREIGN PATENT DOCUMENTS 67214 6/1969 Fed. Rep. of Germany .
86/01813 3/1986 PCT Int'l Appl. .

OTHER PUBLICATIONS

Introduction to Polymer Science and Technology: An SPE Textbook edited by H. S. Kaufman, pp. 267–279.
Thromboresistant, Radioopaque, Softenable Thermoplastic Catheter Compound with Shape Memory Properties, Ward et al.
Softenable, Shape Memory Thermoplastics for Biomedical Use—Robert S. Ward, Plastics Technology, Aug. 1985.

Primary Examiner—Stephen C. Pellegrino
Assistant Examiner—Ralph Lewis
Attorney, Agent, or Firm—Edith A. Rice; Herbert G. Burkard

[57] ABSTRACT

The invention relates to a catheter assembly comprising a cannula, needle and catheter inserter wherein the inserter is in slidable relationship to the cannula and wherein the inserter or other device also serves to selectively restrict the cannula and needle from sliding relative to the inserter. The restricted movement is caused by a portion of the cannula swelling when contacted by a liquid. The invention also relates to a method of inserting a cannula into a living subject using an inserter which is positioned such that the desired length of cannula for initial insertion extends beyond the inserter. The method also relates to further inserting the cannula into the living subject after initial insertion of the cannula.

35 Claims, 10 Drawing Figures

ADJUSTABLE CATHETER ASSEMBLY

BACKGROUND OF THE INVENTION (a) The Invention

The invention relates to a catheter assembly and a method for inserting a cannula useful for the introduction of nutrients or medication, or the extraction of fluids from a living subject. The catheter assembly more particularly comprises a cannula, needle and catheter inserter which allows the selection of the desired length of cannula to be inserted. The method particularly relates to a method of inserting a cannula into a living subject to a desired length.

(b) Background Information

A number of catheter assemblies are known for introduction of a polymeric cannula into a vein, artery or cavity of a living subject for infusion or extraction of fluids.

In one method, a steel needle is sized to fit within the duct of a cannula and is inserted from the proximal end of the cannula so that the needle exits the distal end. The needle is then inserted into the living subject after which the needle is removed from the cannula, leaving the cannula behind with at least its distal end in the subject. Additional tubing can be attached thereto or medicaments or nutrients can be caused to flow through the cannula into the subject.

In order to prevent the needle from sliding relative to the cannula on insertion, several catheter inserters have been developed which aid the person inserting the cannula to prevent such sliding. This also provides a way to control the cannula without contaminating it. Inserters of a type comprising a positionally fixed device having a pair of winged members which when folded up will pinch the needle and prevent motion of the needle relative to the cannula and catheter inserter are known. Generally a relatively stiff cannula of a material to be inserted into the subject such as TEFLON (from DuPONT) is fixed to the distal end of the inserter, while a flexible tubing (e.g. polyvinyl chloride) is attached to the proximal end of the inserter in flow communication with the cannula.

For example, in U.S. Pat. No. 4,194,504 a winged catheter inserter fixed to a cannula is described comprising a resilient tubular body having a lumen and a pair of wings having substantially uniform thickness such that on folding up of the wings, the lumen changes shape to capture the needle within for easier insertion. See also U.S. Pat. Nos. 4,198,973; 4,192,304; 4,192,305; 4,300,553; 4,388,074; 4,445,893; 4,353,369; and 4,326,519.

A difficulty with this type of winged inserter is that the length of cannula to be inserted is limited. The length is predetermined by the position that the inserter has been fixed on the cannula material. The winged inserters of the prior art have been attached to the cannula for a number of reasons including the need to secure cannula at one end of the inserter and flexible tubing at the other end and to prevent the relative movement of the inserter after use. Relatively long lengths of cannula cannot be used with this type of inserter because the inserter must be affixed relatively close to the distal end for accurate control of the cannula and only that portion extending from the distal end of the inserter may be used. Another difficulty with the fixed wing inserter is the desirability of being able to differ the length of the needle and the cannula for ease of insertion into the subject. A person inserting such cannulae, such as a nurse or doctor, will have varying preferences as to the positioning of the inserter relative to the needle and cannula end. This requires stocking several different sizes of cannula fabricated with differing distal end lengths.

One method of overcoming the difficulty of inserting a variable or relatively long length of cannula (greater than about 50 mm) has been to select a needle with an inner diameter greater than the outer diameter of the cannula. The needle is inserted into the subject and the cannula is fed through the needle into the subject to the desired length. This technique has several difficulties. First, the cannula for insertion must be stiff and/or have a wire running through its duct during insertion. Also, when inserting such a device into an area such as a blood vessel, removal of the needle allows blood to escape around the insertion site or possible infection to enter through the insertion site which is larger than the cannula. After the cannula is in the desired position, the needle is generally removed. There is difficulty in removing the needle without further escape of blood or chance of infection. This is especially true when the cannula is attached to a hub portion which prevents sliding the needle off of the cannula's proximal end. If the needle is allowed to remain on the cannula there can be difficulty in preventing the sharpened edge of the needle from further piercing the subject or piercing the cannula. Bulky containment mechanisms are used to minimize but not eliminate this danger. The alternative to this type of method is direct surgical implantation of a cannula in the desired area which is both traumatic and costly.

In summary the prior art to date has encountered great long standing difficulty in inserting a desired length of cannula initially or relatively long lengths of cannula after insertion of the distal end of a cannula. The present invention is directed to overcoming one or more of the problems as set forth above.

SUMMARY OF THE INVENTION

One aspect of the invention relates to a catheter assembly comprising:

a cannula having a distal end portion, a proximal end portion, and a longitudinal duct therethrough from the distal end portion to the proximal end portion;

a needle having a distal and a proximal end and having a sharpened insertion tip at the distal end, the needle being positioned within the distal end portion of the longitudinal duct of the cannula with the insertion tip extending beyond the distal end of the cannula; and a catheter inserter having inserter distal and proximal ends and having a cannula guide channel extending from the inserter distal end to the inserter proximal end, the cannula being positioned in slidable relationship through the channel such that the distal end portion of the cannula extends beyond the distal end of the channel; and a means for selectively restricting the cannula and needle from sliding relative to the channel.

Another aspect of the invention relates to a method comprising:

(a) selecting a catheter assembly comprising:

a cannula having a distal end portion, a proximal end portion, and a longitudinal duct therethrough from the distal end portion to the proximal end portion;

a needle having a distal and a proximal end and having a sharpened insertion tip at the distal end, the needle being positioned within the distal end portion of the longitudinal duct of the cannula with the insertion tip extending beyond the distal end of the cannula; and a catheter inserter having inserter distal and proximal ends and having a cannula guide channel extending from the inserter distal end to the inserter proximal end, the cannula being positioned in slidable relationship through the channel such that the distal end portion of the cannula extends beyond the distal end of the channel; and a means for selectively restricting the cannula and needle from sliding relative to the channel;

(b) positioning the inserter on the cannula such that the desired length of the distal end of the cannula extends beyond the distal end of the channel;

(c) engaging the means such that the cannula and the needle are restricted from sliding relative to the channel;

(d) inserting the needle and the cannula partially into the living subject.

Yet another aspect of the invention relates to a catheter assembly comprising:

a cannula having a distal end portion, a proximal end portion, and a longitudinal duct therethrough from the proximal end portion to the distal end portion, the cannula being formulated of a material selected such that an outer circumference thereof increases when at least a part of the distal end portion thereof is inserted into a living subject and maintained in said living subject, and/or when the duct is contacted by an aqueous liquid, for a period of time sufficient for the increased outer circumference to form;

an inserter having a guide channel therethrough in which the cannula slidably fits when the cannula has the smaller outer circumference and by which the cannula is non-slidably held when the cannula has the increased outer circumference; and means for selectively restricting the cannula from sliding relative to the channel when the cannula has the smaller outer circumference.

Still another aspect comprises a catheter assembly comprising:

a cannula having a distal end portion, a proximal end portion, and a longitudinal duct therethrough from the proximal end portion to the distal end portion, the cannula being formulated of a material selected such that it has a 2.5% secant modulus which decreases (a) on exposure to temperature of from about 20° C. to about 40° C.; and/or (b) upon insertion of a part of the distal end portion of the cannula into a body of a living subject and maintained therein; and/or (c) when the duct of the cannula is contacted by a liquid, for a period of time; such that the cannula softens with a softening ratio of at least 2:1;

an inserter having a guide channel therethrough in which the cannula slidably fits; and means for selectively restricting the cannula from sliding relative to the channel when the cannula has the smaller outer diameter.

DETAILED DESCRIPTION OF THE INVENTION

Figure 1:
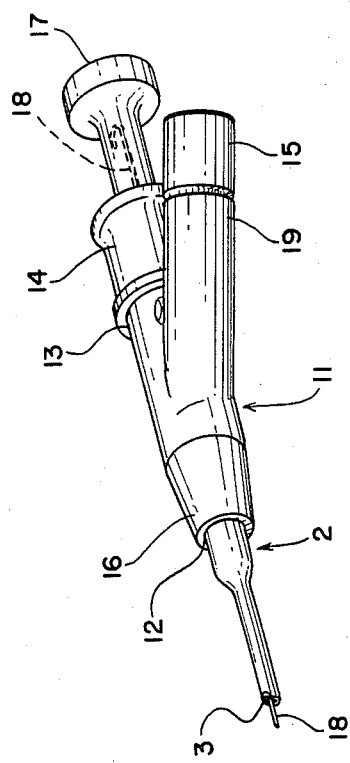
FIG. 1 is a perspective view of a catheter assembly of the invention with a slidable inserter having preferred embodiments including a hub, penetrable polymeric sealing member over one proximal end of the hub and an additional port for introduction or withdrawing of liquids.

The catheter assembly of the invention comprises a cannula of a desired length, a needle and a slidable inserter. In a preferred embodiment, the catheter assembly comprises a cannula of a desired length with an outer circumference which increases, and/or of a material whose 2.5% Secant modulus decreases, and a slidable inserter and optionally a protective sheath.

The cannula of the invention can be any material suitable for introduction into a living subject. Preferably these materials are polymeric in nature and are selected to be sufficiently stiff for insertion but still relatively flexible such as fluoroethylene propylene (e.g. FEP-TEFLON from DuPONT) or the like. In general, the cannula should have a 2.5% Secant Modulus greater than about 20,000 N/cm$^2$ and preferably greater than about 28,000 N/cm$^2$ to prevent buckling or wrinkling upon insertion into the subject. Even more preferred are those compositions which soften or exhibit a decreased 2.5% Secant Modulus for example by exposure to liquids or upon insertion of the distal end portion of the cannula into the body of a living subject and maintained therein or upon exposure to a temperature of from about 20° C. to about 40° C. Particulary preferred compositions absorb liquid (e.g. hydration) and thereafter soften to a 2.5% Secant modulus of less than 7,000 N/cm$^2$ which reduces the trauma to the surrounding tissues of the subject. The term softening ratio is used herein to refer to the ratio of the 2.5% Secant modulus values of the composition selected in the form of a tubular cannula initially to the 2.5% Secant modulus of the composition when softened. It is preferred that at least a portion of such compositions are hydrophilic. It is also preferred that the composition soften with a softening ratio of at least about 2:1.

Examples of softening polymers useful in the practice of the invention are those described in commonly assigned copending application serial number 780,543 filed Sept. 26, 1985, incorporated herein by reference. The preferred composition for the cannula comprises (a) a first phase which comprises a substantially non-hydrophilic polymeric component; and (b) a second phase which comprises a hydrophilic polymeric component;

said material (i) being capable of absorbing water to an extent that it softens with a softening ratio of at least about 2:1 and/or swells with a swelling ratio of at least about 1.3:1; and (ii) when substantially completely hydrated, having an energy to break of at least about 700 N-cm/cm$^3$ and a 2.5% Secant Modulus of less than about 7,000 N/cm$^2$.

Also useful are those softening polymers, described in U.S. Pat. Nos. 4,359,558, 4,424,305, 4,454,309 and 4,439,583 to Tyndale Plains-Hunter Ltd. incorporated herein by reference. The preferred cannula composition essentially comprises a polyurethane diacrylate composition having from about 90 to about 65 weight percent of a hydrophilic polyurethane resin and from about 10 to about 35 weight percent of a diacrylate.

An alternative material which may be utilized as the cannula material is a thermoplastic composition with softenable and/or shape-memory properties. Such polymeric compositions are described, for example, in the following articles: Softenable, Shape-Memory Thermoplastics For Biomedical Use, Robert S. Ward, MD7D, August 1985; and Thromboresistant, Radiopaque, Softenable Thermoplastic Catheter Compound With Shape-Memory Properties, R. S. Ward, K. A. White, J. S. Riffle, Second World Congress On Biomaterials, 10th Annual Meeting Of The Society For Biomaterials, Washington, D.C., April 27–May 1, 1984. The aforementioned thermoplastic compositions comprise a base polymer that is a block or segmented co-polymer thermoplastic with at least one block type which has an abrupt effective glass transition temperature ($T_g$) at or greater than room temperature, but less than approximately body temperature. The remainder of the base polymer contains hard blocks whose dominant thermal transition is substantially greater than body temperature. The cannulae can also be made to expand and soften as follows. The cannulae are originally made with their eventually desired expanded internal diameter and then are heated above the glass transition ($T_g$), drawn out to form longer and thinner cannulae and held in this state until cooled below the ($T_g$). Once the longer and thinner cannulae have warmed to a temperature that is greater than room temperature but less than approximately body temperature, i.e., once the cannulae have reached the glass transition temperature, ($T_g$), the shape-memory properties operate and the cannulae increase in internal and external diameter while shrinking in length.

It is also preferred when selecting such softening materials that cannulae of such material also swell wherein at least a portion of the cannula inner cross-section of the duct and/or outer circumference of the cannula increases to form an enlarged inner cross-section of the duct and/or enlarged outer circumference of the cannula when inserted in a living subject and maintained therein and/or when the duct is contacted by a liquid for a period of time sufficient for the enlarged duct cross-section and/or outer circumference to form. Preferably the duct cross-section increases to from about 25% to about 400%.

The composition of the cannula may be crosslinked if desired. Crosslinking gives the composition strength above the melting or softening points of the uncross-linked polymeric components permitting sterilization of the catheter assembly using a cannula of such composition at above such temperature. Crosslinking of the material selected for the cannula may also be used to adjust the 2.5% secant modulus of the composition to a desired value. Crosslinking may also increase the tensile energy to break of the material which has been softened. Cross-linking can also be used to minimize extractable components of the composition.

Crosslinking can be effected by use of an appropriate crosslinking agent or by irradiation, preferably in the presence of a crosslinking promoter, such as triallyl isocyanurate or the like. In a preferred embodiment the material is crosslinked by high energy gamma or beta radiation.

The material of the cannula may contain additional ingredients such as stabilizers, antioxidants, radiopacifiers, medicaments, fillers or the like. For certain applications it may be advantageous to incorporate a water soluble or water dispersable medicament which can leach from the material when it contacts the fluids of the living subject. Such medicaments include anti-thrombogenic agents, antibiotics, antiviral agents, anticoagulants, anti-inflammatory agents or the like.

A cannula selected such that it swells or softens should not do so appreciably during the time it is being inserted in a living subject or the like. It is preferable that such swell or softening time should preferably be at least about 15 seconds and preferably at least about 60 seconds. The swelling of the cannula has several advantages. Swelling of the cannula permits insertion of a smaller device for equivalent fluid flow and/or can result in pressure around a wound site reducing bleeding and bacterial invasion into the wound and prevent catheter slipout, a common cause for changing catheters prematurely. Increased cross-section of the cannula duct also permits increased flow through the cannula when compared with similar non-swelling cannula of identical initial dimensions. This allows access to smaller areas such as the veins in the limbs and easier insertion into the selected site. Further, swelling of the cannula may increase the outer circumference sufficiently that it becomes as great as the diameter of the inserter channel. After insertion of the cannula this may be desirous. The inserter then loses its ability to slide relative to the cannula and needle due to the pressure of the cannula against the inserter channel. This is advantageous in preventing relative movement of the cannula or inserter. Once the inserter is attached (e.g. by taping) to the subject, further movement of the cannula in or out of the subject is limited. Cannulae which become soft are also advantageous. A soft cannula tends to cause less irritation to the intima (lining of the vein), to the insertion site and is less likely to contribute to mechanical phlebitis. The softness of the cannula also permits it to float in a vein rather than lie on the point where inserted and consequently any infusion is delivered evenly helping to avert chemical phlebitis.

Once the cannula is selected, a needle is selected having a distal and proximal end and having a sharpened insertion tip at the distal end. The needle may be selected to be either hollow or solid. The needle is positioned within the distal end portion of the longitudinal duct of the cannula with the insertion tip extending beyond the distal end of the cannula. An extraction wire, rod, etc. may optionally be attached to the proximal end of the needle and extend outward to the proximal end of the cannula. Extraction of the needle may be accomplished by pulling on the extraction wire. Alternately, the proximal end of the needle may extend beyond the inserter toward the proximal end of the the cannula for ease of extraction.

Finally, a catheter inserter having distal and proximal ends and having a cannula guide channel extending from the distal end to the proximal end of the inserter has a cannula positioned in slidable relationship through the channel such that the distal end portion of the cannula extends beyond the distal end of the channel. Means are provided for selectively restricting the cannula and needle from sliding relative to the channel. In its preferred embodiment the catheter inserter comprises a body having a pair of members extending therefrom, the members being movable to selectively restrict the cannula and needle from sliding relative to the channel. In a more preferred embodiment the body has a pair of flexible wing members extending therefrom, the wings being foldable upward together to selectively restrict the cannula and needle from sliding relative to the channel. In another more preferred embodiment the members are moved from a relaxed positioned to a tensed position to selectively restrict the cannula and needle from sliding relative to the channel. The body of catheter inserter will preferably have a bore extending from the distal end to the proximal end of the inserter and which serves as the guide channel. The diameter of the guide channel will preferably be at least equal to or slightly larger than the outer circumference of the cannula. In any event, the cannula and channel will be such that the cannula can be positioned in slidable relationship to the channel. Preferred catheter inserters resemble the winged inserters of the prior art but have relatively larger longitudinal bores and comprise a continuous cannula extending beyond the distal end of the inserter to beyond the proximal end of the inserter to allow a slidable relationship with the cannula. Other inserters would include tubular devices with an enlarged bore for positioning the cannula and an area which could be manually squeezed, have a hose clamp attached thereover, or have a means tightened thereon to restrict the cannula sliding relative to the channel. Another method of obtaining the slidable relationship is to use an inserter such as a spring which is normally closed and prevents the slidable relationship and must be opened to achieve the slidable relationship.

In particular, the catheter assembly of the invention is useful for inserting a cannula in a living subject. Preferably the cannula is inserted in a blood vessel or cavity. The preferred use of the catheter assembly is for intravenous (IV) use. By living subject is meant any living thing, e.g. mammal, reptile, fish, etc. for which fluids are necessary to infuse or drain. In particular the assembly is useful in mammals particularly, horses, cattle, dogs, cats and humans.

The catheter assembly may be used at this stage to infuse or drain liquids or to hook or connect to other apparatus or devices or used to position sensors or the like.

In a preferred embodiment the catheter further comprises a cannula hub portion. The hub portion has a passageway therethrough from the proximal end to the distal end of the hub and has an attaching means for attaching the proximal end portion of the cannula to the distal end of the hub with the passageway in flow communication with the duct in the proximal end portion of the cannula. Many such hubs are known in the prior art and are suitable for the invention. Where the cannula material is a swellable material it is desirable to have a hub assembly which will prevent restriction of flow in the cannula and will accommodate the expansion. One such hub is described in commonly assigned U.S. patent application Ser. No. 788,461 filed Oct. 17, 1985, incorporated herein by reference.

Preferably the cannula hub portion has a hub portion having a hub passageway therethrough from a first to a second end thereof, wherein the hub passageway has a cross-sectional area throughout at least substantially equal to the enlarged duct cross-section and which further comprises an attaching means for attaching the proximal end portion of the cannula to the first end of the hub with the passageway through the hub in flow communication with the duct in the proximal end portion of the cannula, the attaching being in a manner such that the cross-sectional area of the duct adjacent to the proximal end portion, following formation of the enlarged duct cross-section, is throughout at least substantially equal to the enlarged duct cross-section along the remainder of the cannula.

The opening at the proximal end of the hub may be sealed by use of a penetrable polymeric sealing member. The sealing member will be useful in preventing escape of fluids from the subject. Additionally, the sealing member can be used to introduce fluids for example by inserting the needle of a syringe through the penetrable member. Yet another use for a polymeric sealing member would be to prevent fluid loss when a needle extraction wire is withdrawn from the proximal end of the hub. The hub portion may also be designed with any fitting or attachment means for attaching tubing or the like in flow communication with the hub passageway (e.g. luer lock hub). It may also be desirous that more than one opening in the proximal end of the hub will be in flow communication with the hub passageway (e.g. FIG. 1). This is useful to connect one constant source of fluid (e.g. an IV drip bottle) and leave a different site accessible for single injection of additional fluid or medicaments.

When a long section of cannula is to be inserted into the living subject, care must be used in maintaining sterility of the portion of cannula initially positioned at the proximal end of the inserter. Contact of the cannula by the users fingers or the like would contaminate the cannula making it unsuitable for use in a living subject. One solution to this problem is to enclose the proximal portion of the cannula that is to be handled in an axially collapsible cover for example, a polyethylene bag of a very flexible material or a more rigid polymeric material with accordian-type folds which allow axial collapsing, such that the cannula may be inserted further by handling the cover.

Another solution to the problem is to cover a portion of the cannula with an axially non-collapsible sheath. By axially non-collapsible is meant that when pushing in the cannula for to further insertion while also grasping the sheath, the sheath does not buckle or wrinkle or the like to an appreciable amount. The sheath, however, has walls which are of a relatively flexible material. The sheath has both a distal end and a proximal end. There is further, a longitudinal slit at least a portion of the way through the wall of the sheath. In another embodiment the slit does not extend all the way through the wall of the sheath prior to removal to further aid in the protecting of the cannula. The cannula is positioned within the duct of the sheath in the area to be protected. The sheath is capable of being opened along the longitudinal slit and removed from the cannula. In a preferred embodiment there is a means for aiding in the opening of the longitudinal slit. This means may be a part of the inserter (as in FIG. 8) which opens the sheath during insertion of the cannula or an added device which opens the sheath during insertion. The inserter is preferably made of a polymeric material. Preferred polymeric materials include polyvinyl chloride (PVC), polyurethane and fluoroethylene propylene.

The sheath may further comprise indicators (FIG. 10) positioned such that upon insertion of the cannula and corresponding removal of the sheath the indicators indicate the depth to which the cannula has been inserted.

Once the catheter assembly is selected and made, the method of the invention may be used to insert the cannula into a living subject. The method further comprises positioning the inserter on the cannula such that the desired length of the distal end of the cannula extends beyond the distal end of the channel. In general from about 12 mm to about 50 mm of cannula will be so positioned for insertion. This may be accomplished for example by sliding the inserter to the desired position. This is advantageous over fixed inserters which require stocking of different desired lengths. Next the inserter means is engaged such that the cannula and the needle are restricted from sliding relative to the channel. In the preferred embodiment this is accomplished by folding the flexible wing members of the preferred inserter upward (see Figures) such that the inserter means is engaged. The needle and cannula distal ends may then be inserted into the living subject by grasping the inserter and pushing the needle into the desired area.

Once the cannula is inserted as desired the inserter means may be disengaged. At this point it is desirous that the needle be removed to prevent any damage to the subject or cannula. The needle may be withdrawn at least a portion toward and preferably out the proximal end portion of the cannula. This is preferably accomplished by pulling on an extraction wire attached to the proximal end of the needle as described earlier.

The cannula may also be inserted further into the subject (before swelling where appropriate) by grasping the hub at the cannula in the area between the proximal end of the cannula and the proximal end of the inserter and pushing in the direction of insertion. Where a protective cover is used, the protective cover is grasped firmly enough to grasp both the cover and cannula for further insertion.

Once this is accomplished fluids may be drained or introduced into the subject as desired, for example, wound drainage, IV drip bottles, syringe injection and the like.

Referring now to the drawings. FIG. 1 relates to a catheter assembly of the invention comprises cannula distal (1) and proximal (2) ends which have longitudinal duct (3) therein. Positioned in the longitudinal duct is a needle (4) having a sharpened end (5). Inserter (6) comprising distal end (7) and proximal end (8), has a bore (9) therethrough of a diameter about equal to or greater than the outer diameter of the cannula. The inserter also has a means for restricting the relative movement of the cannula and needle relative to the inserter which comprises wings (10) which can be folded upward to be engaged. The needle also has extraction wire (18) attached to its proximal end extended out the penetrable polymeric member (14) to a knob (17) for grabbing the wire. The hub (11) of FIG. 1 has a bore (12) from the distal end (16) to the proximal end (13 and 19) in fluid communication with the cannula duct. Proximal end (19) can be used to introduce tubing and the like by removal of plug (15) in the proximal end passageway.

Figure 2:
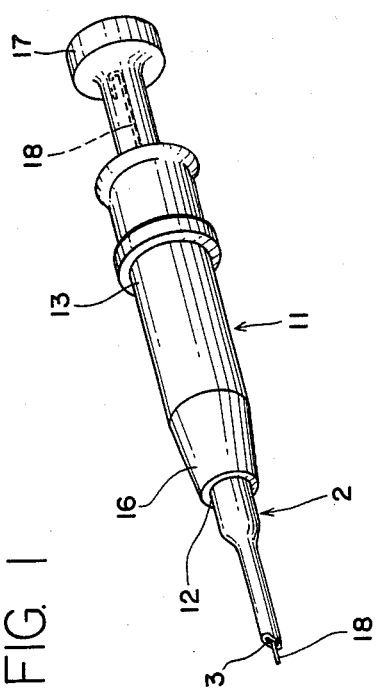
FIG. 2 is a perspective view of another embodiment of the invention comprising a hub, slidable inserter, cannula and needle.

In FIG. 2, all the numbers refer to identical portions except that FIG. 2 has a hub with only a single proximal end (13) in fluid communication with the cannula.

Figure 3:
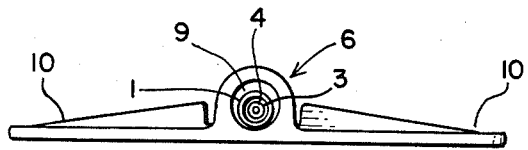
FIG. 3 is a cross-sectional view of the catheter assembly through the catheter inserter.

FIG. 3 is a cross-sectional view of the catheter inserter (6) with wing members (10) and bore (3) having cannula (1) and needle (4) positioned therein.

Figure 4:
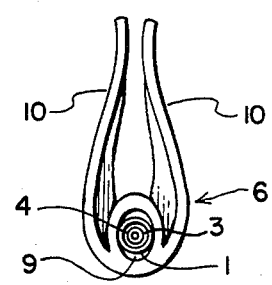
FIG. 4 is a cross-sectional view of the catheter assembly through the catheter inserter which is engaged to restrict the cannula and needle from sliding relative to the inserter.

FIG. 4 is similar to FIG. 3 except the wings (10) have been folded upward to engage which restricts the cannula and needle from sliding relative to the inserter.

Figure 5:
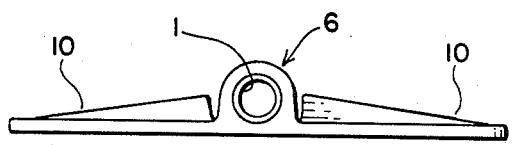
FIG. 5 is a cross-sectional view of the catheter assembly through the catheter inserter with no needle and the outer diameter of the cannula which has increased to restrict the cannula from sliding relative to the inserter.

FIG. 5 is similar to FIG. 3 except that the needle has been removed and the cannula has swollen such that its outer diameter is about equal to the diameter of the bore.

Figure 6:
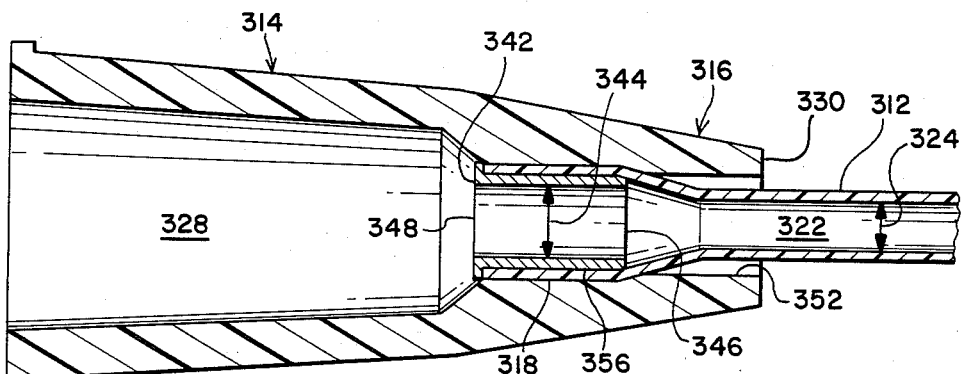
FIG. 6 is a cross-sectional view with an embodiment of a hub and cannula whose outer circumference is capable of expanding.
Figure 7:
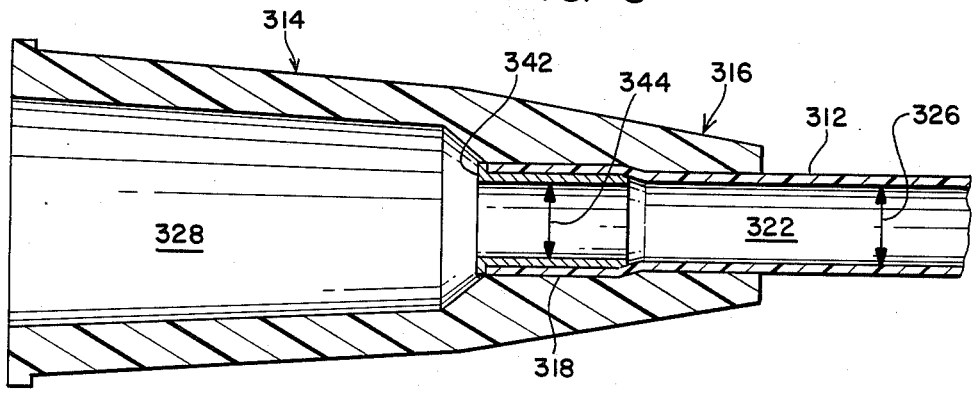
FIG. 7 is a cross-sectional view similar to FIG. 6 but with the cannula in the expanded state.

Referring now to FIG. 6 and 7, there is illustrated a particular embodiment of the present invention which includes a hub insert 342 for use with an expanding cannula. In the embodiment in FIG. 6 the hub insert has an opening 344 therethrough from a first end 346 to a second end 348 thereof. The opening 344 has inner cross-section which is throughout at lest substantially equal to 125% of the initial duct cross-section 324 and is preferably at least substantially equal to the enlarged duct cross-section (FIG. 7). A part 352 of the passageway 328 in the hub 319 adjacent the first end 330 of the hub 314 has an inner surface which is geometrically similar to and positioned about an outer surface 356 of the hub insert 342. The part 352 of the passageway 328 and the outer surface 356 of the hub insert 342 are adapted to hold the proximal end portion 318 of the cannula 312 impressed therebetween. If desired, a bonding composition can be attached between the hub insert 342 and the duct 322 and/or between the port 352 of the passageway 328 and the outer surface of the proximal end portion 318 of the cannula 312. FIG. 6 illustrates an embodiment wherein the cannula 312 is in the non-expanded state and has not yet expanded. The proximal end portion 318 of the cannula 312 has been positioned over the hub insert 342, thus preshaping or preforming it only adjacent to the hub insert 342. Alternatively, the proximal end portion 318 may be thermally or otherwise preshaped if preferred. FIG. 7 illustrates the embodiment wherein the cannula is in the expanded state.

Figure 8:
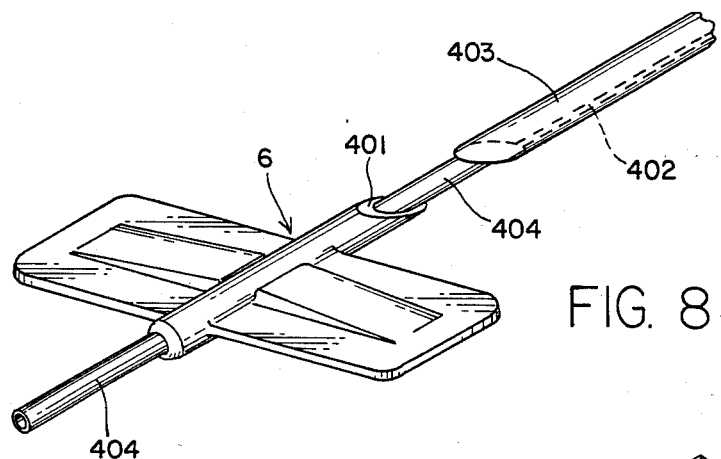
FIG. 8 is a perspective view of a portion of a catheter assembly showing a further embodiment of the invention wherein a portion of the cannula is covered with a protective sheath.
Figure 9:
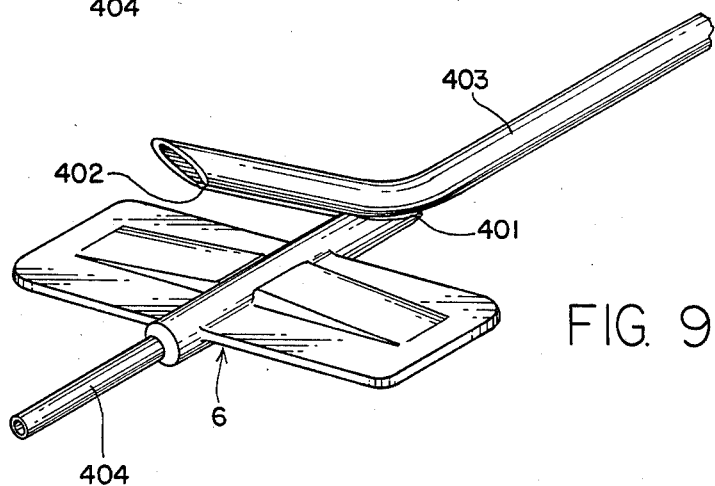
FIG. 9 is a view similar to FIG. 8 but with the sheath in the process of removal.

Referring to FIGS. 8 and 9 we see a portion of a perspective view of a catheter assembly with an inserter 6. On the cannula 404 is a protective sheath 403 with a longitudinal slit 402 for removing the sheath 403. In order to help open the cannula along the longitudinal slit, a means 401 is provided on the inserter such that on pushing the sheath towards the means the sheath opens along the slit and is removed from the catheter assembly or further depicted in FIG. 9.

Figure 10:
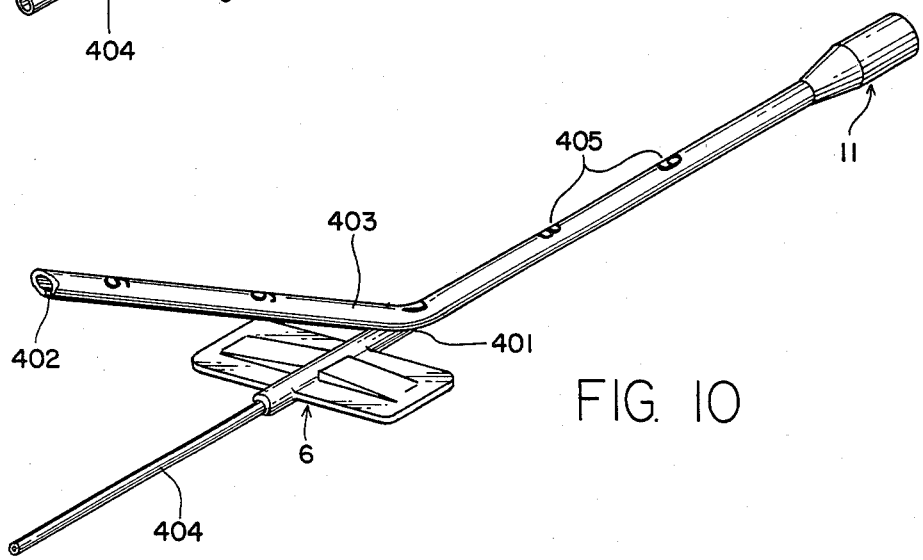
FIG. 10 is a perspective view of a complete catheter assembly similar to FIG. 9 where the sheath has indicator markings for insertion depth.

Referring to FIG. 10, we see an entire perspective view of a catheter assembly with protective sheath being removed as in FIG. 9. The protective sheath in FIG. 10 has additional indicators 405 which indicate the depth to which the cannula has been inserted.

What is claimed is:

1. A catheter assembly, comprising:
   a cannula having a distal end portion, a proximal end portion, and a longitudinal duct therethrough from the distal end portion to the proximal end portion;

a needle having a distal and a proximal end and having a sharpeded insertion tip at the distal end, the needle being positioned within the distal end portion of the longitudinal duct of the cannula with the insertion tip extending beyond the distal end of the cannula;

a catheter inserter having inserter distal and proximal ends and having a cannula guide channel extending from the inserter distal end to the inserter proximal end, the cannula being positioned in slidable relationship through the channel such that the distal end portion of the cannula extends beyond the distal end of the channel; and a means for selectively restricting the cannula and needle from sliding relative to the channel;

wherein at least a portion of the cannula is of a material selected such that an outer circumference of the duct increases to form an enlarged outer circumference such that it restricts the cannula from sliding relative to the channel when at least a part of the distal end portion of the cannula is inserted into a body of a living subject and maintained therein and/or when the duct is contacted by a liquid, for a period of time sufficient for the enlarged outer diameter to form.

2. A catheter assembly, according to claim 1, wherein the cannula guide channel comprises a bore extending from the distal end to the proximal end of the inserter.

3. A catheter assembly according to claim 1, wherein the catheter inserter comprises a body having a pair of members extending therefrom, the members being movable to selectively restrict or release the cannula and needle from sliding relative to the channel.

4. A catheter assembly according to claim 1, wherein at least a portion of the cannula is of a material selected such that an inner cross-section of the duct increases to form an enlarged duct cross section when at least a part of the distal end portion of the cannula is inserted into a body of a living subject and maintained therein and/or when the duct is contacted by a liquid, for a period of time sufficient for the enlarged duct cross-section to form.

5. A catheter assembly according to claim 4, wherein the inner cross-section of the duct increases when the duct is contacted by an aqueous liquid.

6. A catheter assembly according to claim 4, wherein the increase in the duct cross-section is from about 25% to about 400%.

7. A catheter according to claim 4 which further comprises a cannula hub portion having a hub passageway therethrough from a first to a second end thereof, wherein the hub passageway has a cross-sectional area throughout at least substantially equal to the enlarged duct cross-section and which further comprises an attaching means for attaching the proximal end portion of the cannula to the first end of the hub with the passageway through the hub in flow communication with the duct in the proximal end portion of the cannula, the attaching being in a manner such that the cross-sectional area of the duct adjacent the proximal end portion, following formation of the enlarged duct cross-section, is throughout at least substantially equal to the enlarged duct cross-section along the remainder of the cannula.

8. A catheter assembly according to claim 1, wherein at least a portion of the cannula is of a material selected such that it has 2.5% secant modulus which decreases
(a) on exposure to temperature of from about 20° C. to about 40° C.; and/or (b) upon insertion of a part of the distal end portion of the cannula into a body of a living subject and maintained therein; and/or (c) when the duct of the cannula is contacted by a liquid, for a period of time;

such that the cannula softens with a softening ratio of at least 2:1.

9. A catheter assembly according to claim 8, wherein the 2.5% secant modulus of the cannula decreases when the cannula is contacted by an aqueous liquid.

10. A catheter assembly according to claim 8, wherein at least a portion of the cannula is selected of a material comprising a thermoplastic composition with an effective glass transition temperature of greater than room temperature but less than about the body temperature of the living subject into which the cannula is to be inserted.

11. A catheter assembly according to claim 10, wherein the thermoplastic composition further has shape memory properties.

12. A catheter assembly according to claim 1 which further comprises a cannula hub portion having a passageway therethrough from the proximal end to the distal end of the hub, and having an attaching means for attaching the proximal end portion of the cannula to the distal end of the hub with the passageway in flow communication with the duct in the proximal end portion of the cannula.

13. A catheter assembly according to claim 12, wherein the hub has a penetrable polymeric sealing member positioned to seal the proximal end of the hub.

14. A catheter assembly according to claim 12, wherein the hub has a connection means at the proximal end of the hub for attaching tubings or fitting in flow communication with the hub passageway.

15. A catheter according to claim 12, wherein the needle or an extraction wire that is attached to the proximal end of the needle extends through the longitudinal duct of the cannula distally to the hub passageway and out the proximal end of the hub.

16. A catheter assembly according to claim 15, wherein the hub has a connection means at the proximal end of the hub for attaching tubings or fittings in flow communication with the hub passageway.

17. A catheter assembly according to claim 1, wherein the needle or an extraction wire attached to the proximal end of the needle extends through the longitudinal duct of the cannula and out the proximal end of the cannula.

18. A catheter assembly according to claim 1, wherein the distal end portion of the cannula is of a material having a 2.5% secant modulus greater than about 20,000 N/cm$^2$.

19. A catheter assembly according to claim 1, wherein at least a portion of the cannula is selected of a material comprising a thermoplastic composition with an effective glass transition temperature of greater than room temperature but less than about the body temperature of the living subject into which the cannula is to be inserted.

20. A catheter assembly according to claim 19, wherein the thermoplastic composition further has shape memory properties.

21. A catheter according to claim 1, wherein the cannula comprises a material with hydrophilic properties.

22. A catheter according to claim 21 wherein the cannula comprises:

(a) a first phase which comprises a substantially non-hydrophilic polymeric component; and (b) a second phase which comprises a hydrophilic polymeric component;

said material (i) being capable of absorbing water to an extent that it softens with a softening ratio of at least about 2:1 and/or swells with a swelling ratio of at least about 1.3:1; and (ii) when substantially completely hydrated, having an energy to break of at least about 700 N-cm/cm$^3$ and a 2.5% Secant modulus of less than about 7,000 N/cm$^2$.

23. A catheter assembly to claim 21, wherein the cannula comprises a graft or block copolymer with hydrophilic segments with a softening ratio of at least 2:1.

24. A catheter according to claim 23, wherein the cannula comprises a polyurethane diacrylate composition having from about 90 to about 65 weight percent of a hydrophilic polyurethane resin and from about 10 to about 35 weight percent of a diacrylate.

25. A method of inserting a catheter into a living subject comprising:

(a) selecting a catheter assembly, comprising:

a cannula having a distal end portion, a proximal end portion, and a longitudinal duct therethrough from the distal end portion to the proximal end portion;

a needle having a distal and a proximal end and having a sharpened insertion tip at the distal end, the needle being positioned within the distal end portion of the longitudinal duct of the cannula with the insertion tip extending beyond the distal end of the cannula;

a catheter inserter having inserter distal and proximal ends and having a cannula guide channel extending from the inserter distal end to the inserter proximal end, the cannula being positioned in slidable relationship through the channel such that the distal end portion of the cannula extends beyond the distal end of the channel; and a means for selectively restricting the cannula and needle from sliding relative to the channel;

(b) positioning the inserter on the cannula such that the desired length of the distal end of the cannula extends beyond the distal end of the channel;

(c) engaging the means such that the cannula and the needle are restricted from sliding relative to the channel; and (d) inserting the needle and the cannula partially into the living subject;

wherein at least a portion of the cannula is of a material selected such that an outer circumference of the duct increases to form an enlarged outer circumference such that it restricts the cannula from sliding relative to the channel when at least a part of the distal end portion of the cannula has been inserted into the living subject and maintained therein for a period of time sufficient for the enlarged outer diameter to form.

26. A method according to claim 25, which further comprises the step of disengaging the inserter means.

27. A method according to claim 25, which further comprises the steps of inserting the cannula further into the living subject to the desired length.

28. A method according to claim 25, wherein the cannula is a material selected such that it has 2.5% secant modulus which decreases.

(a) on exposure to temperature of from about 20° C. to about 40° C.; and/or (b) upon insertion of a part of the distal end portion of the cannula into a body of a living subject and maintained therein; and/or (c) when the duct of the cannula is contacted by a liquid, for a period of time;

such that the cannula softens with a softening ratio of at least 2:1.

29. A method according to claim 25 which further comprises the step withdrawing the needle at least a portion of the way toward the proximal end portion of the cannula.

30. A method according to claim 29 wherein the needle is withdrawn by pulling on an extraction wire attached to the proximal end of the needle.

31. A method according to claim 25 wherein the inserter comprises a body having a pair of members extending therefrom, the inserter means being movable to selectively restrict or release the cannula and needle from sliding relative to the channel.

32. A method according to claim 25 wherein the cannula is of a material selected such that the outer circumference increases when at least a part of the distal end portion of the cannula is inserted into a body of a living subject and maintained therein and/or when the duct is contacted by a liquid, for a period of time sufficient for the enlarged outer circumference to form such that it selectively restricts the cannula from sliding relative to the channel.

33. A method according to claim 25 wherein the cannula and the needle are inserted into a blood vessel of a living subject.

34. A method according to claim 25, wherein the cannula and the needle are inserted into a cavity of a living subject.

35. A method according to claim 25, including the added steps of:

(e) attaching the mechanical means to the living subject adjacent the point of insertion of the cannula; and (f) maintaining the distal end portion of the cannula partially in the living subject for a desired period of time.

* * * * *